United States Patent [19]
Javier, Jr. et al.

[11] Patent Number: 6,093,177
[45] Date of Patent: *Jul. 25, 2000

[54] CATHETER WITH FLEXIBLE INTERMEDIATE SECTION

[75] Inventors: Manuel A. Javier, Jr., Santa Clara; Stephen B. Pearce, Fremont; Sam G. Payne, Santa Clara; Randy J. Kesten, Mountain View, all of Calif.

[73] Assignee: Cardiogenesis Corporation, Santa Clara, Calif.

[ * ] Notice: This patent issued on a continued prosecution application filed under 37 CFR 1.53(d), and is subject to the twenty year patent term provisions of 35 U.S.C. 154(a)(2).

[21] Appl. No.: 08/813,503

[22] Filed: Mar. 7, 1997

[51] Int. Cl.$^7$ ................................................ A61M 25/00
[52] U.S. Cl. ............................................ 604/280; 604/264
[58] Field of Search ................................... 604/282, 280, 604/264; 606/15

[56] References Cited

U.S. PATENT DOCUMENTS

| | | |
|---|---|---|
| 4,651,751 | 3/1987 | Swendson et al. . |
| 4,739,768 | 4/1988 | Engelson ................................. 604/282 |
| 4,784,639 | 11/1988 | Patel . |
| 4,983,169 | 1/1991 | Furukawa . |
| 4,997,431 | 3/1991 | Isner et al. ................................. 606/15 |
| 5,222,949 | 6/1993 | Kaldany . |
| 5,358,493 | 10/1994 | Schweich, Jr. et al. ................ 604/264 |
| 5,437,632 | 8/1995 | Engelson ................................... 604/53 |
| 5,531,721 | 7/1996 | Pepin et al. ............................. 604/282 |
| 5,569,218 | 10/1996 | Berg . |
| 5,658,263 | 8/1997 | Dang et al. ............................. 604/280 |
| 5,911,715 | 6/1999 | Berg et al. ............................. 604/525 |

FOREIGN PATENT DOCUMENTS

| | | |
|---|---|---|
| WO 92/15356 | 9/1992 | WIPO . |
| WO 96/38194 | 12/1996 | WIPO . |
| WO 98/38925 | 9/1998 | WIPO . |

*Primary Examiner*—Michael Powell Buiz
*Assistant Examiner*—Julian W. Woo
*Attorney, Agent, or Firm*—Heller Ehrman White and McAuliffe LLP

[57] ABSTRACT

An intraluminal catheter with an elongated tubular shaft with proximal, intermediate, and distal shaft sections for positioning a therapeutic or diagnostic device within a patient's body region such as a heart chamber. The intermediate shaft section has greater flexibility than the proximal or distal shaft sections, and is preferably of sufficient flexibility to easily assume the curvature of the patient's aortic arch, and reduce the force of contact between the catheter distal end and tissue defining the patient's body region to thereby reduce restriction on the rotation of the catheter. The flexible intermediate shaft section is preferably of a length to occupy a significant portion of the aortic arch, and the catheter overall length is preferably sufficient to have a catheter proximal extremity extending out of the patient and a distal extremity extending at least into an aortic passageway adjacent the patient's left ventricle.

50 Claims, 2 Drawing Sheets

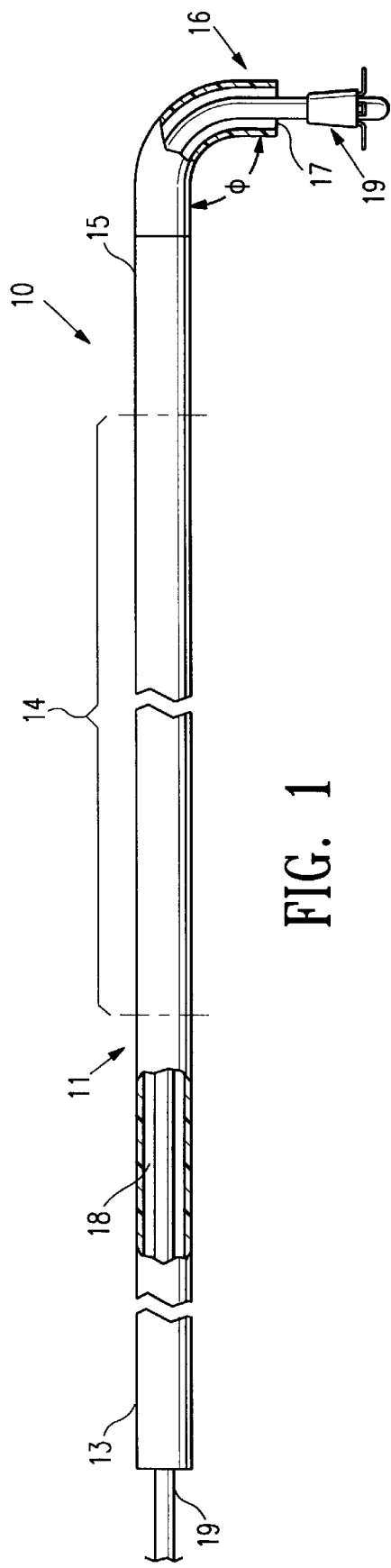
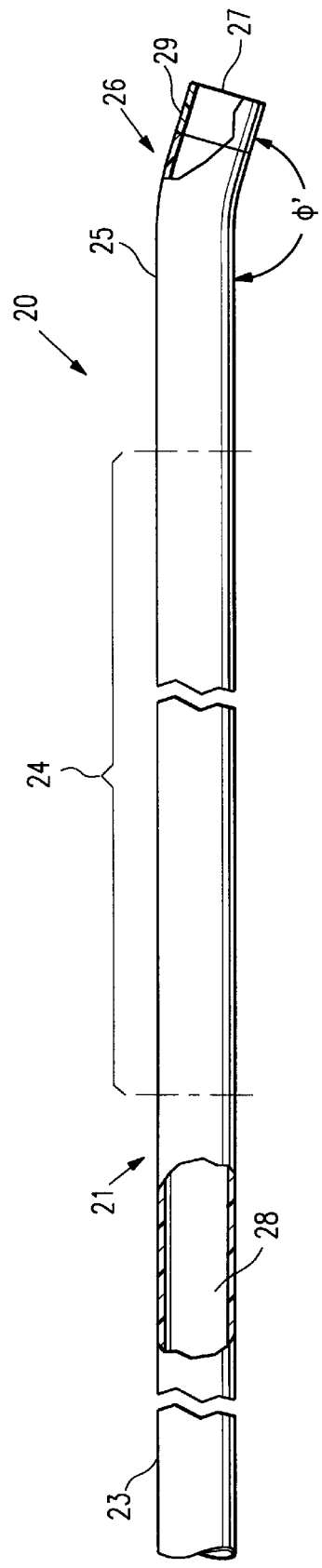

CATHETER WITH FLEXIBLE INTERMEDIATE SECTION

BACKGROUND OF THE INVENTION

This invention is directed to an elongated catheter adapted to facilitate delivery of a therapeutic or diagnostic device into a body cavity such as the left ventricle of a patient's heart, and particularly for the treatment of myocardial tissue experiencing ischemic conditions by revascularization of such tissue.

Myocardial revascularization typically involves formation of one or more channels in a patient's heart wall defining the heart chamber to treat a patient's ischemic myocardial tissue therein. The first trials of the revascularization process was made by Mirhoseini et al. See for example the discussions in *Lasers in General Surgery* (Williams & Wilkins; 1989), pp 216–223. Another early disclosure of this procedure is found in U.S. Pat. No. 4,658,817 (Hardy). Both of these references describe revascularization procedures which require the chest wall to be opened and which include formation of the revascularization channels through the epicardium, myocardium and endocardium, i.e. the entire heart wall.

Copending application Ser. No. 08/368,409, filed on Dec. 30, 1994, which is incorporated herein in its entirety, describes an intravascular system for percutaneous transmyocardial revascularization (PTMR) which is introduced into a peripheral artery and advanced through the patient's arterial system into the left ventricle of the patient's heart. The revascularization channels are formed through the endocardium and into the myocardium from within the left ventricle. This procedure eliminates the need of the prior intraoperative procedures which require opening the chest cavity and penetrating the entire heart wall to form a channel through the endocardium into the myocardium.

While the percutaneous method and system for introducing the revascularization device developed by Aita et al. was a substantial advance, one of the difficulties in forming revascularization channels from within a patient's left ventricle by means of a percutaneously introduced revascularization system was to accurately direct the distal tip of the channel forming device to a desired region of the patient's endocardium and to maintain the placement of the distal end of the channel forming device against a desired region of the ventricular wall at a proper angle while the heart was beating. Copending application Ser. No. 08/646,856 filed May 8, 1996, which is incorporated herein in its entirety, describes an intravascular system using one or more delivery catheters which may have a preshaped or shapeable distal extremities to facilitate directing a therapeutic or diagnostic device slidably disposed within the catheter lumen toward the region of the endocardium where the procedure is to be performed.

What has been needed is a guiding or delivery catheter with the maneuverability desired for advancing through the patient's vasculature yet having sufficient strength and rigidity to support a channel forming device within the patient's heart chamber. The present invention satisfies these and other needs.

SUMMARY OF THE INVENTION

The present invention is directed to intraluminal catheters which aid in positioning a therapeutic or diagnostic device within a patient's body region such as a heart chamber. The intraluminal catheter of the invention generally has an elongated tubular shaft with proximal, intermediate, and distal shaft sections. The intermediate shaft section has greater flexibility than the proximal or distal shaft sections. The distal shaft section may have equal or greater flexibility than the proximal shaft section.

The relative flexibility or the inverse stiffness of the various shaft sections may be achieved with conventional techniques used in catheter design, including selection of materials and wall thickness, and the use of reinforcing means such as strands, coils and the like. For example, a thin walled intermediate shaft section would have high flexibility relative to thicker walled proximal or distal shaft sections made from the same or similar materials. Alternatively, the material used in the intermediate shaft section may be inherently more flexible than a different material used in the proximal or distal shaft sections. Likewise, the catheter shaft sections may be formed of the same material with the distal and proximal sections provided with reinforcing stands or coils.

In accordance with one aspect of the invention, the intraluminal catheter is a delivery catheter for directing an elongated intraluminal device to a desired region within the patient's body such as the patient's heart chamber. The catheter shaft has proximal and distal ends, and a lumen extending to and in fluid communication with a port in the distal end of the catheter. The port and inner lumen are configured to slidably receive an elongated therapeutic or diagnostic device. A typical delivery catheter device of the invention is particularly suitable for delivery of an elongated device for forming a channel into the wall defining the heart chamber or a device for performing other ablation treatments and diagnosis.

For the percutaneous delivery of therapeutic or diagnostic devices into a patient's left ventricle the delivery catheter is of a length sufficient to have a proximal extremity extending out of the patient and a distal extremity extending into the patient's left ventricle. The overall length of the catheter is preferably about 100 cm to about 120 cm, and typically about 105 cm. The length of the intermediate section is about 5 to about 50 cm, and preferably about 20 cm to about 30 cm, so that it extends through at least a substantial portion of a human patient's aortic arch. The length of the distal section is about 2 to about 10 cm, and preferably about 4 cm to about 8 cm to ensure that the distal end of the catheter shaft extends into the left ventricle of the patient's heart. Therefore, the intermediate shaft section is a length at least about 2 to about 8, and preferably about 4 times the length of the distal shaft section.

In a presently preferred embodiment, the distal shaft section is relatively short when compared to the intermediate shaft section. Additionally, the proximal shaft section is relatively long compared to the intermediate and distal shaft sections. When the distal end of the catheter has been advanced through a patient's aortic passageway and into the left ventricle or slightly downstream thereof, the more flexible intermediate shaft section occupies aortic arch, or at least a significant portion thereof, slightly downstream of the aortic valve. The relatively stiff proximal shaft section extends from the proximal extremity of the delivery catheter outside the patient to a point within the descending aorta downstream of the aortic arch. The distal shaft section extends from the flexible intermediate shaft section to the distal end of the delivery catheter within the left ventricle.

The catheter of the invention is particularly suitable for delivery of therapeutic or diagnostic devices such as laser based optical fiber systems for forming channels within the wall of the patient's heart, i.e. PTMR. The optical fiber system which is adapted to emit laser energy from its distal end, is slidably disposed within the lumen of the delivery catheter and is of a length sufficient to extend out the port in the distal end of the catheter to engage tissue of the endocardium while forming the channel or performing other types of procedures. The distal end of the catheter is preferably shaped so that when positioned within the patient's heart chamber, it provides the desired orientation for the delivered therapeutic or diagnostic device toward the region of the endocardium where the procedure is to be performed.

The delivery catheter of the invention may be advanced through a previously introduced guiding catheter which has a lumen in fluid communication with a port in the distal end of the catheter. In accordance with one aspect of the invention, the guiding catheter of the invention itself has a flexible intermediate shaft section between less flexible proximal and distal shaft sections, in the same or similar manner as the delivery catheter. The discussion above relating to the relative flexibility and length of the proximal, intermediate, and distal sections on the delivery catheter applies equally well for the corresponding sections on the guiding catheter of the invention. Whether the guiding catheter is advanced until its distal end is disposed within the left ventricle or at least within the ascending aortic passageway downstream of the left ventricle, the flexible shaft section is sized and positioned on the catheter to occupy a significant portion of the aortic arch. A nontraumatic distal tip may be provided on the guiding catheter in a conventional manner.

In one presently preferred method of practicing the invention, the delivery catheter is percutaneously introduced into a patient's peripheral artery, such as the femoral artery, and advanced through the patient's arterial system until the distal end is disposed within the patient's left ventricle or slightly downstream of the aortic valve in the ascending aorta. The delivery catheter may be advanced over a guidewire or within a guiding catheter previously introduced which has a distal extremity positioned within the left ventricle or within the ascending aorta slightly downstream of the aortic valve. When myocardial revascularization is to be performed, an intravascular device having a means to form channels in the patient's heart wall is advanced through the lumen of a properly positioned delivery catheter until the operative end of the device is positioned at a desired location within the patients heart. The position of the delivery catheter and the intravascular device may be adjusted to precisely access a desired region of the endocardium.

Providing a flexible intermediate shaft section on a catheter between the stiffer proximal and distal shaft sections of the catheter facilitates passage of the catheter through the aortic passageway. Catheter designs without this flexible section will have difficulty advancing through the aortic arch, and will likely contact the aortic wall. The result of the contact with the aortic wall can be trauma to the wall and frictional drag on the catheter hindering its maneuverability. Catheter designs with flexibility in the distal region that is uniform or ever increasing towards the distal tip fail to provide the torque control and kink resistance inherent in the design of the invention. Moreover, when contact with the heart wall does result, catheters having a flexible intermediate shaft section will produce lower point loads against the wall than would be produced by conventional catheters.

The flexible intermediate shaft section reduces the combined system stiffness of a delivery catheter within a guiding catheter. This, along with a reduction in the pushing force produced from contact of the catheter distal end with the heart wall, lowers the force against the heart wall and the drag on rotation of the catheter. Unlike the catheter of the invention, conventional catheters in contact with a heart wall produce a significant pushing force against the heart wall which restricts the freedom of rotation of the catheter. These and other advantages of the invention will become more apparent from the following detailed description of the invention and the accompanying exemplary drawings.

BRIEF DESCRIPTION OF THE DRAWINGS

FIG. 1 is an elevational view, partially in section, of a delivery catheter which embodies features of the invention with a revascularization device therein.

FIG. 2 is an elevational view, partially in section, of a guiding catheter which embodies features of the invention.

DETAILED DESCRIPTION OF THE INVENTION

Figure 5:
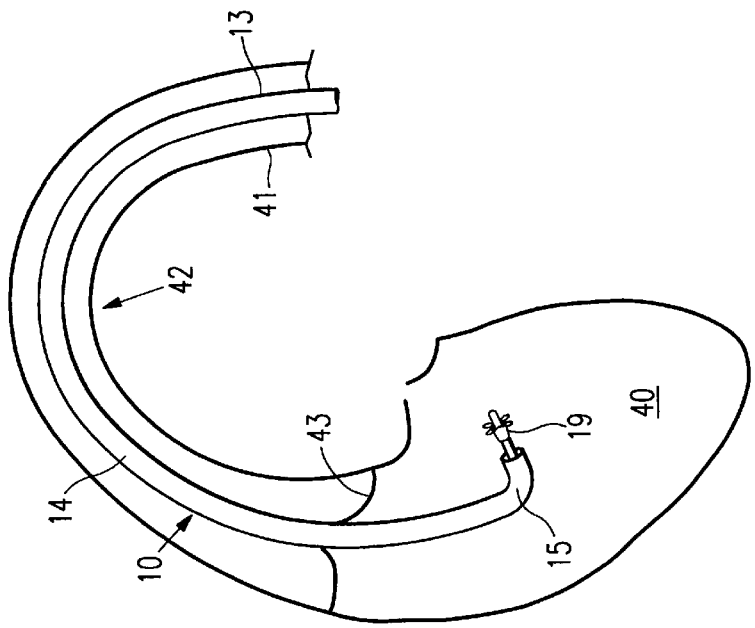
FIG. 5 illustrates the position of the assembly similar to that shown in FIG. 3 except that a guiding catheter is not present. The flexible intermediate shaft section of the delivery catheter is shown disposed in the aortic arch.

As shown in FIG. 1, the delivery catheter 10 of the invention generally includes an elongated shaft 11, a proximal shaft section 13, an intermediate shaft section 14, and a distal shaft section 15. The distal shaft section 15 has a distal end 16 with a port 17 in fluid communication with a lumen 18 extending through the catheter shaft 11. A therapeutic or diagnostic device 19, such as an ultrasonic, laser, or electrode based device for tissue ablation or sensing, is slidably disposed within the lumen 18 of the delivery catheter 10. In FIG. 1 the therapeutic device 19 illustrated is a revascularization device, such as described in copending application Ser. No. 08/584,957 (M. A. Javier, Jr. et al.) filed on Jan. 11, 1996, which is incorporated herein by reference.

FIG. 2 illustrates a guiding catheter 20 embodying features of the invention which generally includes an elongated shaft 21, a proximal shaft section 23, an intermediate shaft section 24, and a distal shaft section 25. The distal shaft section 25 has a distal end 26 which includes a nontraumatic distal tip 29. A port 27 is provided on the distal tip 29, which is in fluid communication with a lumen 28 extending through the catheter shaft 21. The lumen 28 is configured to slidably receive the delivery catheter 10 and therapeutic or diagnostic device 19 therein.

FIGS. 1 and 2 illustrate presently preferred embodiments of the delivery and guiding catheter in which the distal shaft sections, 15 and 25 respectively, are bent at an angle, $\phi$ and $\phi'$ respectively. However, the distal extremity of the delivery and guiding catheters of the invention may contain a variety of shapes conventional in catheter design.

Figure 4:
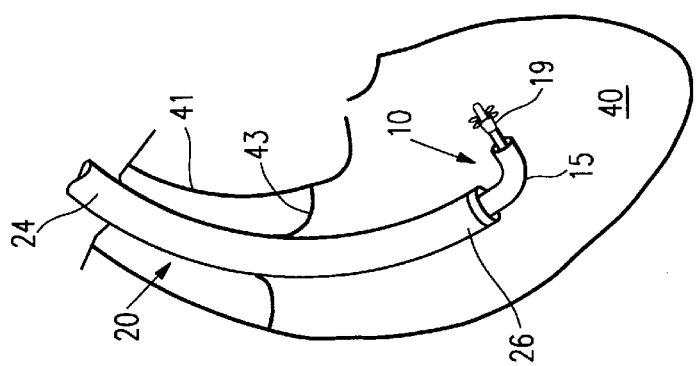
FIG. 4 illustrates the position of the assembly similar to that shown in FIG. 3 except that the guiding catheter extends within the left ventricle and the distal extremity of the delivery catheter system is disposed more centrally within the left ventricle.
Figure 3:
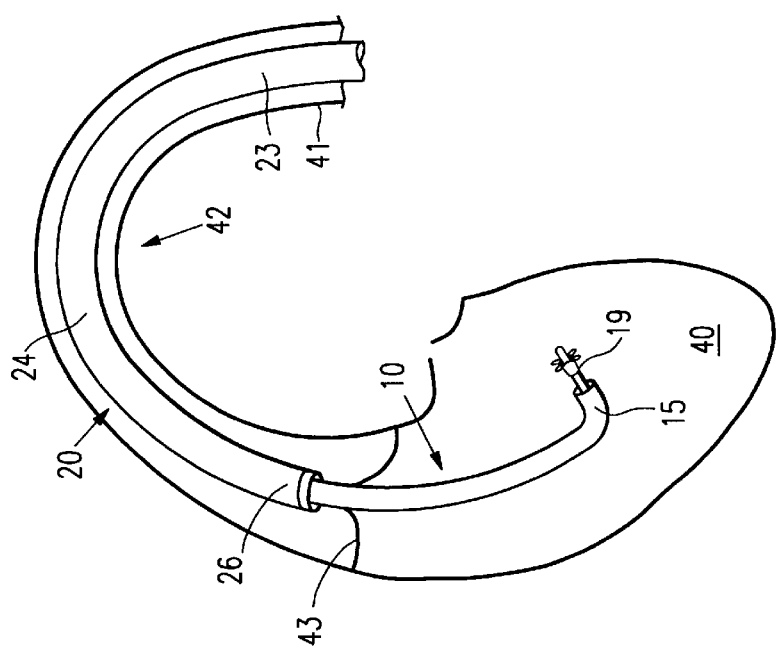
FIG. 3 illustrates the positioning of the assembly of an embodiment of the invention within the patient's left ventricle and aortic arch with the distal extremity of the guiding catheter within the ascending aortic passageway and the distal extremity of the delivery catheter within the left ventricle and a revascularization device positioned against a patient's heart wall. The flexible intermediate section of the guiding catheter is shown disposed in the aortic arch.

FIGS. 3 and 4 illustrate the placement of the catheter system of the invention within the patient, with the delivery catheter 10 slidingly disposed within the lumen 28 of the guiding catheter 20 and the therapeutic device 19 extending into the patient's left ventricle 40. In FIG. 3, the guiding catheter 20 is shown within the patient's ascending aorta 41. The guiding catheter 20 is positioned so that the intermediate shaft section 24 occupies the aortic arch 42, and the guiding catheter distal end 26 is within the ascending aorta 41 downstream of the left ventricle 40 and aortic valve 43. FIG. 4 illustrates the guiding catheter 20 extending into the left ventricle 40. Although the guiding catheter 20 may be advanced into the left ventricle 40 as shown in FIG. 4, the intermediate shaft section 24 is sized so that it still occupies a significant portion of the aortic arch 42 (not shown).

In FIG. 5, the delivery catheter 10 shown in FIG. 3 is illustrated without a guiding catheter 20, and is positioned so that the intermediate shaft section 14 occupies the aortic arch 42.

FIGS. 3 and 5 illustrate presently preferred embodiments of the guiding catheter and delivery catheter, respectively, in which the length of the distal shaft sections 25 and 15 is relatively small compared to the length of the intermediate shaft sections 24 and 14 respectively. The overall length of the delivery catheter 10 is typically 5 cm to about 30 cm longer than the guiding catheter to ensure that the proximal end 13 and distal end 15 of the delivery catheter extend out the guiding catheter 20 proximal end 23 and distal end 25 respectively, to control the direction and location of the distal end of the delivery catheter by manipulation of the proximal end of the delivery catheter from outside of the patient's body.

The delivery catheter 10 and guiding catheter 20 intermediate shaft sections 14 and 24 are constructed to be relatively flexible compared to the proximal and distal shaft sections, to facilitate advancement of the catheters through the ascending aorta 41. The proximal and distal shaft sections have stiffnesses of about 2, preferably about 3 times that of the flexible intermediate shaft section. A method of measuring the desired stiffness which has been found suitable is a modification of ASTM test D747. This modification measures the load required to deflect a cantilevered specimen 12.7 mm from the fixed end a distance of 1 mm. For the intermediate shaft section of the delivery catheter, a suitable load is about 5 to about 30 gms, preferably about 10 to 20 gms. For the proximal and distal stiff shaft sections, the loads should range about 20 to 70 gm, preferably about 30 to 50 gms. Guiding catheters are generally stiffer than the delivery catheters and the load ranges about 60 to about 200 gms, preferably about 100 to 150 gms for the proximal and distal shaft sections, and about 30 to 100 gms preferably about 50 to 80 gms for the flexible intermediate shaft sections. In a presently preferred embodiment, the load values of the proximal and distal shaft sections of a catheter are substantially similar. However, it may be desirable to have a proximal shaft section with a higher load value, i.e., greater stiffness, than the distal shaft section. The various catheter shaft sections may be formed of conventional materials providing the desired flexibility and strength characteristics. For example, the delivery catheter 10 intermediate shaft section 14 may be a relatively flexible material such as PEBAX 55D, and the proximal and distal shaft section may be a high strength, stiff material such as PEBAX 72D or nylon, and is preferably PEBAX 72D. The wall thickness of the intermediate shaft section may be about 0.050 mm to about 0.20 mm less than the wall thickness of the proximal and distal shaft sections to provide an intermediate shaft section with the desired flexibility relative to the other shaft sections.

In a presently preferred method of the invention, the guiding catheter 20 is first introduced into the patient's arterial system and advanced through the system until the distal end 26 is disposed at the desired location either within the ascending aorta 41 downstream of the left ventricle 40 or within the left ventricle 40. When the guiding catheter 20 is in place, the intermediate shaft section 24 will occupy a significant portion of the aortic arch. The delivery catheter 10 and therapeutic or diagnostic device 19 may then be advanced together or sequentially through the guiding catheter 10 into the left ventricle 40, at which point intermediate shaft section 14 occupies the aortic arch 42 as well. The delivery catheter 10 may be rotated, or advanced and retracted to position the distal end at the desired region of the endocardium. The diagnostic or therapeutic device 19 may then be advanced out the port 17 in the distal end 16 of catheter to a point adjacent to the endocardium of the patient's heart. After the procedure the device may be withdrawn or repositioned within the left ventricle 40. FIG. 5 illustrates an alternative method of practicing the invention in which the delivery catheter 10 has been advanced through the patient's arterial system to the ascending aorta 41 without the aid of a guiding catheter, possibly using a guidewire (not shown).

While the present invention is described herein in terms of certain preferred embodiments, those skilled in the art will recognize that various modifications and improvements may be made to the invention without departing from the scope thereof.

What is claimed is:

1. An intraluminal catheter for positioning a therapeutic or diagnostic device within a patient's body cavity, comprising:
    a) a tubular proximal shaft section;
    b) a tubular intermediate shaft section being distal to the proximal shaft section, having a flexibility that is greater than that of the proximal shaft section, and having a length less than the proximal shaft section;
    c) a tubular distal shaft section being distal to the intermediate shaft section, having a distal end, having a flexibility that is less than that of the intermediate shaft section and having a length less than the intermediate shaft section;
    d) a port in the distal end of the distal shaft section; and
    e) a lumen which is configured to receive a therapeutic or diagnostic device and which extends to and in fluid communication with the port in the distal end of the distal shaft section.

2. The intraluminal catheter of claim 1 wherein the catheter is a delivery catheter.

3. The intraluminal catheter of claim 1 wherein the catheter is a guiding catheter.

4. The intraluminal catheter of claim 1 wherein the intermediate shaft section has a length at least about 2 to about 8 times the length of the distal shaft section.

5. The intraluminal catheter of claim 1 wherein the intermediate shaft section has a length about 4 times the length of the distal shaft section.

6. The intraluminal catheter of claim 1 wherein the intermediate shaft section has a length of about 5 to about 50 cm.

7. The intraluminal catheter of claim 1 wherein the intermediate shaft section has a length of about 20 to about 30 cm.

8. The intraluminal catheter of claim 1 wherein the intermediate shaft section has a length capable of occupying a significant portion of an aortic arch of the patient.

9. The intraluminal catheter of claim 1 wherein the distal shaft section has a shape at the distal end configured to facilitate directing an intravascular device disposed within the lumen of the catheter to a desired region within the body cavity.

10. The intraluminal catheter of claim 1 wherein the distal shaft section includes a nontraumatic distal tip.

11. The intraluminal catheter of claim 1 wherein the catheter has a length sufficient to have a proximal extremity extending out of the patient and a distal extremity extend at least into an ascending aortic passageway adjacent a left ventricle of the patient.

12. The intraluminal catheter of claim 1 wherein the intermediate section has a flexibility capable of allowing the intermediate section to assume a curvature of an aortic arch without the catheter exerting significant pressure on a wall defining the patient's body cavity.

13. The delivery catheter of claim 2 wherein the intermediate shaft section has a flexibility such that a load of about 5 to about 30 grams is required to deflect a cantilevered length of the catheter shaft 12.7 mm from the fixed end a distance of 1 mm.

14. The delivery catheter of claim 2 wherein the intermediate shaft section has a flexibility such that a load of about 10 to about 20 grams is required to deflect a cantilevered length of the catheter shaft 12.7 mm from the fixed end a distance of 1 mm.

15. The delivery catheter of claim 2 wherein the proximal and distal shaft sections have a flexibility such that a load of about 20 to about 70 grams is required to deflect a cantilevered length of the catheter shaft 12.7 mm from the fixed end a distance of 1 mm.

16. The delivery catheter of claim 2 wherein the proximal and distal shaft sections have a flexibility such that a load of about 30 to about 50 grams is required to deflect a cantilevered length of the catheter shaft 12.7 mm from the fixed end a distance of 1 mm.

17. The delivery catheter of claim 2 wherein the lumen is configured to slidably receive a diagnostic or therapeutic device.

18. The guiding catheter of claim 3 wherein the intermediate shaft section has a flexibility such that a load of about 60 to about 200 grams is required to deflect a cantilevered length of the catheter shaft 12.7 mm from the fixed end a distance of 1 mm.

19. The guiding catheter of claim 3 wherein the intermediate shaft section has a flexibility such that a load of about 100 to about 150 grams is required to deflect a cantilevered length of the catheter shaft 12.7 mm from the fixed end a distance of 1 mm.

20. The guiding catheter of claim 3 wherein the proximal and distal shaft sections have a flexibility such that a load of about 30 to about 100 grams is required to deflect a cantilevered length of the catheter shaft 12.7 mm from the fixed end a distance of 1 mm.

21. The guiding catheter of claim 3 wherein the proximal and distal shaft sections have a flexibility such that a load of about 50 to about 80 grams is required to deflect a cantilevered length of the catheter shaft 12.7 mm from the fixed end a distance of 1 mm.

22. The guiding catheter of claim 3 wherein the lumen thereof is configured to slidably receive a delivery catheter.

23. A catheter system for performing diagnostic or therapeutic procedures within a patient's body, comprising:
   a) a guiding catheter;
   b) a delivery catheter slidably disposed within the guiding catheter lumen, comprising:
      i) a tubular proximal shaft section;
      ii) a tubular intermediate shaft section being distal to the proximal shaft section, having a flexibility that is greater than that of the proximal shaft section;
      iii) a tubular distal shaft section being distal to the intermediate shaft section, having proximal and distal ends, having a port on the distal end, and having a length and a flexibility that are less than that of the intermediate shaft section; and
      iv) a lumen extending to and in fluid communication with the port on the distal end; and
   c) a therapeutic or diagnostic device slidably disposed within the delivery catheter lumen.

24. The catheter system of claim 23 wherein the guiding catheter comprises:
   a) a tubular proximal shaft section;
   b) a tubular intermediate shaft section being distal to the proximal shaft section, having a flexibility that is greater than that of the proximal shaft section;
   c) a tubular distal shaft section being distal to the intermediate shaft section, having proximal and distal ends, and having a flexibility that is less than that of the intermediate shaft section;
   d) a port on the distal end of the distal shaft section; and
   e) a lumen extending to and in fluid communication with the port on the distal end.

25. The catheter system of claim 23 wherein the delivery catheter has an overall length about 5 cm to about 30 cm longer than an overall length of the guiding catheter.

26. A catheter system for performing diagnostic or therapeutic procedures within a patient's body, comprising:
   a) a delivery catheter for positioning a therapeutic or diagnostic device within a patient's left ventricle configured to be slidably advanced over a guidewire, comprising:
      i) a tubular proximal shaft section;
      ii) a tubular intermediate shaft section being distal to the proximal shaft section, having a flexibility that is greater than that of the proximal shaft section and a length of about 4 cm to about 50 cm;
      iii) a tubular distal shaft section being distal to the intermediate shaft section, having a distal end with a port on the distal end, and having a flexibility that is less than that of the intermediate shaft section; and
      iv) a lumen extending to and in fluid communication with the port on the distal end;
   b) a therapeutic or diagnostic device positioned within the delivery catheter lumen and extending out the distal end port.

27. A method for performing a diagnostic or therapeutic procedure within a patient's body, comprising:
   a) advancing a delivery catheter having a proximal shaft section, a flexible tubular intermediate section, and a distal shaft section, wherein said flexible tubular intermediate shaft section has a length of about 4 cm to about 50 cm and occupies a significant portion of the aortic arch, and the distal shaft section of the delivery catheter extends into the patient's left ventricle said distal shaft section having a length and a flexibility less than that of said flexible tubular intermediate section;
   b) advancing an elongated diagnostic or therapeutic device having an operative distal end through the delivery catheter and out a port in a distal end of the delivery catheter so that the operative distal end engages the desired region of the patient's endocardial layer; and c) performing a diagnostic or therapeutic procedure within the left ventricle.

28. The method of claim 27 further including, before step (a), the steps comprising:
    a) providing a guiding catheter having a flexible tubular intermediate shaft section and introducing the guiding catheter into a peripheral artery of the patient;
    b) advancing the guiding catheter through the patient's arterial system until the flexible tubular intermediate shaft section occupies a significant portion of the aortic arch, and until a distal shaft section of the guiding catheter extends at least into an aortic passageway adjacent the patient's left ventricle;
    c) advancing the delivery catheter having a flexible tubular intermediate shaft section through the distal shaft section of the guiding catheter.

29. An intraluminal catheter of claim 1 wherein the distal shaft section has a length of about 2 cm to about 10 cm, and has a flexibility that is less than that of the intermediate shaft section.

30. The intraluminal catheter of claim 29 wherein the catheter is a delivery catheter.

31. The intraluminal catheter of claim 29 wherein the catheter is a guiding catheter.

32. The intraluminal catheter of claim 29 wherein the intermediate shaft section has a length at least about 2 to about 8 times the length of the distal shaft section.

33. The intraluminal catheter of claim 29 wherein the intermediate shaft section has a length about 4 times the length of the distal shaft section.

34. The intraluminal catheter of claim 29 wherein the intermediate shaft section has a length of about 5 to about 50 cm.

35. The intraluminal catheter of claim 29 wherein the intermediate shaft section has a length of about 20 to about 30 cm.

36. The intraluminal catheter of claim 29 wherein the intermediate shaft section has a length sufficient to occupy a significant portion of an aortic arch of the patient.

37. The intraluminal catheter of claim 29 wherein the distal shaft section has a shape at the distal end configured to facilitate directing an intravascular device disposed within the lumen of the catheter to a desired region within the body cavity.

38. The intraluminal catheter of claim 29 wherein the distal shaft section includes a nontraumatic distal tip.

39. The intraluminal catheter of claim 29 wherein the catheter has a length capable of having a proximal extremity extend out of the patient and having a distal extremity extend at least into an ascending aortic passageway adjacent a left ventricle of the patient.

40. The intraluminal catheter of claim 29 wherein the intermediate section has a flexibility capable of allowing the intermediate section to assume a curvature of an aortic arch without the catheter exerting significant pressure on a wall defining the patient's body cavity.

41. The delivery catheter of claim 30 wherein the intermediate shaft section has a flexibility such that a load of about 5 to about 30 grams is required to deflect a cantilevered length of the catheter shaft 12.7 mm from the fixed end a distance of 1 mm.

42. The delivery catheter of claim 30 wherein the intermediate shaft section has a flexibility such that a load of about 10 to about 20 grams is required to deflect a cantilevered length of the catheter shaft 12.7 mm from the fixed end a distance of 1 mm.

43. The delivery catheter of claim 30 wherein the proximal and distal shaft sections have a flexibility such that a load of about 20 to about 70 grams is required to deflect a cantilevered length of the catheter shaft 12.7 mm from the fixed end a distance of 1 mm.

44. The delivery catheter of claim 30 wherein the proximal and distal shaft sections have a flexibility such that a load of about 30 to about 50 grams is required to deflect a cantilevered length of the catheter shaft 12.7 mm from the fixed end a distance of 1 mm.

45. The delivery catheter of claim 2 wherein the lumen is configured to slidably receive a diagnostic or therapeutic device.

46. The guiding catheter of claim 31 wherein the intermediate shaft section has a flexibility such that a load of about 60 to about 200 grams is required to deflect a cantilevered length of the catheter shaft 12.7 mm from the fixed end a distance of 1 mm.

47. The guiding catheter of claim 31 wherein the intermediate shaft section has a flexibility such that a load of about 100 to about 150 grams is required to deflect a cantilevered length of the catheter shaft 12.7 mm from the fixed end a distance of 1 mm.

48. The guiding catheter of claim 31 wherein the proximal and distal shaft sections have a flexibility such that a load of about 30 to about 100 grams is required to deflect a cantilevered length of the catheter shaft 12.7 mm from the fixed end a distance of 1 mm.

49. The guiding catheter of claim 31 wherein the proximal and distal shaft sections have a flexibility such that a load of about 50 to about 80 grams is required to deflect a cantilevered length of the catheter shaft 12.7 mm from the fixed end a distance of 1 mm.

50. The guiding catheter of claim 31 wherein the lumen thereof is configured to slidably receive a delivery catheter.

* * * * *

UNITED STATES PATENT AND TRADEMARK OFFICE
CERTIFICATE OF CORRECTION

PATENT NO.    : 6,093,177
DATED         : July 25, 2000
INVENTOR(S)   : Javier Jr. et al.

It is certified that error appears in the above-identified patent and that said Letters Patent is hereby corrected as shown below:

Column 8,
Line 44, AFTER "HAVING A" AND BEFORE "FLEXIBILITY" INSERT -- LENGTH AND A --.

Signed and Sealed this

Twenty-fifth Day of September, 2001

Attest:

*Nicholas P. Godici*

NICHOLAS P. GODICI
*Attesting Officer*    *Acting Director of the United States Patent and Trademark Office*